(12) United States Patent
Murthy et al.

US008323704B2

(10) Patent No.: US 8,323,704 B2
(45) Date of Patent: Dec. 4, 2012

(54) **PROCESS FOR PREPARATION OF EXTRACT OF *DECALEPIS HAMILTONII* HAVING ANTIOXIDANT ACTIVITY**

(75) Inventors: Kotamballi Nagendra Murthy Chidambara Murthy, Mysore (IN); Giridhar Parvatam, Mysore (IN); Thammannan Rajasekaran, Mysore (IN); Gokare Aswathanarayana Ravishankar, Mysore (IN)

(73) Assignee: Council of Scientific and Industrial Research, New Delhi (IN)

( * ) Notice: Subject to any disclaimer, the term of this patent is extended or adjusted under 35 U.S.C. 154(b) by 1497 days.

(21) Appl. No.: 10/585,226

(22) PCT Filed: Dec. 31, 2003

(86) PCT No.: PCT/IN03/00440
§ 371 (c)(1),
(2), (4) Date: May 30, 2007

(87) PCT Pub. No.: WO2005/063272
PCT Pub. Date: Jul. 14, 2005

(65) Prior Publication Data
US 2008/0003313 A1    Jan. 3, 2008

(51) Int. Cl.
*A61K 36/00* (2006.01)

(52) U.S. Cl. ........................................ 424/725; 424/773
(58) Field of Classification Search ................... None
See application file for complete search history.

(56) References Cited

U.S. PATENT DOCUMENTS
5,445,809 A *   8/1995   Strobel et al. ................ 424/1.81

OTHER PUBLICATIONS

Yanagimoto et al, Antioxidative activities of volatile extracts from green tea, oolong tea and black tea, Journal of Agricultural and Food Chemistry (2003), 51 (25), 7396-7401.*
Giamperi et al, Composition and antioxidant activity of essential oil and ethanolic extract obtained from fresh flowers of *Sambucus nigra*, Rivista italiana EPPOS (2003), 35, 33-40.*
Nagarajan, S. et al., "Chemical Composition of the Volatiles of *Decalepis hamiltonii* (Wight & Arn)," *Flavour and Fragrance Journal*, 16(1):27-29, 2001.
Thangadurai D. et al., "Essential Oil Constituents and in Vitro Antimicrobial Activity of *Decalepis hamiltonii* Roots Against Foodborne Pathogens," *J. Agric Food Chem.* 50(11):3147-9, May 22, 2002.

* cited by examiner

*Primary Examiner* — Qiuwen Mi
(74) *Attorney, Agent, or Firm* — Seed IP Law Group PLLC

(57) ABSTRACT

The present invention relates to a process for the preparation of antioxidant activity rich extracts from tuberous roots of *Decalepis hamiltonii* and the use of said extract as anti-oxidant, free radical scavenger, the extract is having an antioxidant activity in the range of 4 to 47% and also it can serve as better antioxidant since it can prevent more than one type of free radicals unlike other synthetic antioxidants which can quench only one type of radical.

13 Claims, No Drawings

PROCESS FOR PREPARATION OF EXTRACT OF *DECALEPIS HAMILTONII* HAVING ANTIOXIDANT ACTIVITY

FIELD OF THE INVENTION

The present invention relates to a process for the preparation of anti-oxidant activity rich extracts of tuberous roots of *Decalepis hamiltonii* Wight & Arn.

BACKGROUND AND PRIOR ART

The invention is aimed at development of a process for the preparation of antioxidant activity rich extracts of tuberous roots of *Decalepis hamiltonii* Wight & Arn. *Decalepis hamiltonii* Wight & Arn., (swallow root) belonging to Asclepidaceae is a monogeneric climbing shrub native of the Deccan peninsula and forest areas of Western Ghats of India. It finds use as a culinary spice due to its high priced aromatic roots. The roots are markedly fleshy, cylindrical (1-6 cm IN diameter) are characterized by a sarasaparilla like taste accompanied by a tingling sensation on the tongue as described in Wealth of India 1952 (Wealth of India 1952, A dictionary of raw materials, CSIR, New Delhi 3: 24). The roots of *D. hamiltonii* are used as a flavoring principle (Wealth of India, 1990), appetizer (Murthi, P. B. R. and Seshadri, T. R. Proc. Ind. Acad. Sci. 1947; 13A, 221), blood purifier (Jacob, K. C. Madras Agric. Journal. An unrecorded economic product *Decalepis hamiltonii* W & Arn., Family Asclepidaceae 1937; 25; 176), and preservative (Phadke, N.Y., Gholap A. S., Ramakrishnan K, Subbulakshmi G., *J. Food Sci. Technol.* 1994; 31, 472). Similarly the roots of this taxon as described by Nayar et al. (1978) (Nayar R C, Shetty J K P, Mary Z and Yoganrasimhan 1978. Pharmacological studies of root of *Decalepis hamiltonii* W & Arn and comparison with *Hemidesmus indicus* (L.) R.Br. Proc. Indian Acad. Sciences 87 (B): 37-48) are considered as "Sariva Bheda" in Ayurveda where finds use as an alternative to roots of *Hemidesmus indicus* in the preparation of several herbal drugs like Amrutamalaka taila, Drakshadi churna, shatavari rasayana and yeshtimadhu taila. The roots contain 92% fleshy matter and 8% woody core. Of late the highly aromatic roots have been subjected to over exploitation by destructive harvesting that has endangered the survival of this plant. In the earlier reports by George et al. (George, J. Perira, J., Divakar, S., Udayasankar, K and Ravishankar, G. A. *Current Science,* 1999; 77, 501-502) it was observed that the aromatic roots of *D. hamiltonii* proved to be a potent bioinsecticide on storage pests at lethal and sub-lethal levels (Indian Patent No. 1301/Del/98). The supercritical extracts of these roots proved to be potent antimicrobial agents (George, J., Udayasankar, K., Keshava, N and Ravishankar, G. A. *Fitoterapia* 1999; 70, 172-174). George, J., Bais, H. P. and Ravishankar, G. A. (*Current Science,* 2000; 79:894-898) were able to regenerate plantlets of *D. hamiltonii* W & A from leaf callus. Similarly a method for rooting of *Decalepis hamiltonii* for field transfer was reported earlier (Bais H P, Sudha G, Suresh B & Ravishankar G. A, *Curr. Sci,* 2000, 79: 408-410; Obul Reddy, B., Giridhar, P and Ravishankar G. A, *Current Science* 81(11), 2001, 1479-1482). In *Decalepis hamiltonii* the tuberous root extracts contains the flavour compound 2-hydroxy-4-methoxy benzaldehyde as a major compound (97%) which is extractable by steam distillation method and followed by using dichloromethane (Nagaraj an, S., Jaganmohana Rao L., and Gurudutt, K. N., Chemical composition of the volatiles of *Decalepis hamiltonii* (Wight & Arn.,) Flavour and Fragrance Journal. 16: 27, 2001).

Antioxidants are the compounds that when added to food products, especially to lipids and lipid-containing foods, can increase the shelf life by retarding the process of lipid per oxidation, which is one of the major reasons for deterioration of food products during processing and storage. Synthetic antioxidants, such as butylated hydroxyanisole (BHA) and butylated hydroxytoulene (BHT), have restricted to be use in foods as these synthetic antioxidants are suspected to be carcinogenic (Mahavi D. L., Salunkhe D. K., Toxicological aspects of food antioxidants. In: Food Antioxidants: Madhavi, D L., Deshpande S S, Salunkhe D K, eds.; Dekker: New York, 1995; p 267). In general the oxidation of a metabolic process that leads to energy production necessary for essential cell activities. However, metabolism of oxygen in living cells also leads to the unavoidable production of oxygen-derived free radicals, commonly known as relative oxygen species (ROS) (Mccord J. M., Free radicals and pro-oxidants in health and nutrition. *Food Technol.* 48: 106-110., 1994; Adegoke G. O, Kumar M. N, Gopalkrishna A G, Vardaraj M. C., Sambaiah K., Lokesh B. R, Antioxidants and lipid oxidation in foods—a critical appraisal. *J. Food Sci. Technol.* 35: 283-298, 1998), which are involved in the onset of many diseases. These free radicals attack the unsaturated fatty acids of bio-membranes, which result in lipid peroxidation and the destruction of proteins and DNA, which causes a series of deteriorative changes in the biological systems leading to cell inactivation. Thus the identification of antioxidants which can retard the process of lipid peroxidation by blocking the generation of free radical chain reaction, has gained importance in recent years. In living systems, varieties of antioxidant mechanisms play an important role in combating ROS (Aruoma O I, Nutrition and health aspects of free radicals and antioxidants. Food Chem, 32:671-683, 1994). The antioxidants may act by easing the levels of endogenous defenses by up-regulatinig the expression of genes encoding the enzymes such as super oxide dismutase (SOD), catalase or glutathione peroxidase (Halliwell B, Gutteridge J M C. Free Radicals in Biology and Medicine, $2^{nd}$ Edition, Japan Scientific Societies Press: Tokyo, Japan, 1989).

OBJECT OF THE INVENTION

The main object of the present invention is to provide a process for the preparation of antioxidant activity rich extracts of tuberous roots of *Decalepis hamiltonii* Wight & Arn., which obviates the drawback as detailed above.

In another object of the present invention is to assess the anti-oxidant activity of tuberous root extracts of *Decalepis hamiltonii*.

SUMMARY OF THE PRESENT INVENTION

The present invention relates to a process for the preparation of antioxidant activity rich extracts from tuberous roots of *Decalepis hamiltonii* and the use of said extract as antioxidant, free radical scavenger, the extract is having an anti-oxidant activity in the range of 4 to 47% and also it can serve as better antioxidant since it can prevent more than one type of free radicals unlike other synthetic antioxidants which can quench only one type of radical.

DETAILED DESCRIPTION OF THE INVENTION

Accordingly the Present Invention Provides

1) A Process for the preparation of Antioxidant activity rich extracts of tuberous roots of *Decalepis hamiltonii* Wight & Arn., said process comprises:

a) Cleaning and washing of tubers of *Decalepis hamiltonii*, initially by removing surface contamination by soaking the tubers in 200 ml 70-75% alcohol for 5-10 seconds followed by washing with sterile water thrice.
b) The whole tubers or different portions of tubers (tubers with peel, tubers without peel, only the central core or medullary portion, and only the fleshy portion) were made into paste in mixer.
c) Collection of dichloromethane extracts of roots (1:3) ratio.
d) Determination and elucidation of Antioxidant activity of dichlormethane extracts of roots In an embodiment of the present invention a process for collection of dichloromethane extracts of tubers of *Decalepis hamiltonii* was standardized.

In another embodiment of the present invention the dichloromethane extracts were analyzed for assaying antioxidant activity of tuberous root extracts of *Decalepis hamiltonii*.

In another embodiment of the present invention the whole tubers and different parts of tuberous roots of *Decalepis hamiltonii* Wight & Arn., were initially made into paste in mixer and then dichloromethane fractions of these tubers collected and the flavour metabolite 2-hydroxy-4-metoxy benzaldehyde quantified by GC. Later the antioxidant activities of these dichloromethane fractions in ethanol were determined.

In another embodiment of the present invention the use of dichloromethane extract of *Decalepis hamiltonii* having as an anti-oxidant, wherein the said extract is mixed with a pharmaceutically acceptable excipient or an edible item.

Yet in another embodiment of the present invention the anti-oxidant property is preferably free radical scavenging activity.

Still in another embodiment of the present invention the free radical scavenging activity is hydroxyl radical scavenging activity.

Yet in another embodiment of the present invention the extract is obtained from tuberous root.

In another embodiment of the present invention the anti-oxidant activity is in the range of 4-47%.

Still in another embodiment of the present invention the extract is applied in the range of 100 to 1000 ppm.

Yet in another embodiment of the present invention the extract is obtained from medulla of tubers and peel of tubers.

In another embodiment of the present invention the anti-oxidant activity of extract obtained from medulla is in the range of 30 to 45% when applied in a concentration range of 500 to 1000 ppm.

Still in another embodiment of the present invention the anti-radical activity of extract obtained from medulla is in the range of 35 to 46% when applied in a concentration range of 500 to 1000 ppm.

Still in another embodiment of the present invention the hydroxyl scavenging activity of extract obtained from medulla is in the range of 36 to 47% when applied in a concentration range of 100 to 200 ppm.

Yet in another embodiment of the present invention the anti-oxidant activity of extract obtained from peel is in the range of 36 to 47% when applied in a concentration range of 500 to 1000 ppm.

In another embodiment of the present invention the anti-radical activity of extract obtained from peel is in the range of 32 to 48% when applied in a concentration range of 500 to 1000 ppm.

Still in another embodiment of the present invention the hydroxyl scavenging activity of extract obtained from medulla is in the range of 43 to 49% when applied in a concentration range of 100 to 200 ppm.

Yet in another embodiment of the present invention an anti-oxidant composition comprising an effective amount of dichloromethane extract obtained from tuberous roots of *Decalepis hamiltonii* Wight & Arn optionally along with one or more pharmaceutically acceptable excipients.

BRIEF DESCRIPTION OF TABLES

Table 1: Comparison of anti-oxidant activity of different root extracts of *Decalepis hamiltonii* with standard BHA
Table 2: Comparison of anti-radical activity of different root extracts of *Decalepis hamiltonii* with standard D.P.P.H
Table 3: Comparison of hydroxy radical scavenging activity of different root extracts of *Decalepis hamiltonii*.

EXAMPLES

The following examples are given by way of illustration of the present invention Example 1

Fresh tubers of *Decalepis hamiltonii* were collected from local market and sorted out to a required size (approximately 10.0±1.0 cm lengths and 2.0±0.5 cm diameters). The tubers were cleaned off extraneous matter and soil with 2-4 liters of cold water (15±2° C.)/1000 gm tubers. Later they were surface sterilized first with 200 ml of 70% alcohol for 5 seconds followed by washing with sterile water thrice. The surface of the tubers was blotted with sterilized blotting paper. The tubers (whole tubers (A) 606.35 gm; tubers without skin (B) 185 gm; central core or medullary portion (C) 72.40 gm; peel portion (D) 110 gm) were grounded into paste in mixer. The moisture content of the whole tubers and different parts of the tubers was recorded as: whole tubers (A) 74%; tubers without skin (B) 75%; central core or medullary portion (C) 40.23%; peel portion (D) 53.21%. Dichloromethane was added to the root paste (double to the weight of the sample) and left overnight in dark. Later the dichloromethane extract was separated by using the separating funnel. The same is repeated thrice with dichloromethane. Later all the dichloromethane fractions were pooled. Similarly different portions of the tubers were also separately extracted with dichloromethane after preparing their powder extract as said above (for the whole tuber). The same is air dried and finally dissolved in 1 ml ethanol and preserved in low temperature and dark for further analysis. The combined extracts were passed through a funnel containing anhydrous sodium sulphate to remove the water content, concentrated in a flash evaporator and dissolved in 1 ml ethanol and stored in closed vials. Quantification of the flavour compound was determined by gas chromatographic analysis (GC) using flame ionization detection (FID). All the alcohol extracts were finally analyzed for the flavor content 2-hydroxy-4-methoxy benzaldehyde by GC-MS.

Analysis of 2-hydroxy-4-methoxybenzaldehyde (2H4MB) was done by spotting the root, extracts on TLC plate along with standard (Fluka Chemicals, Switzerland) and run in a solvent system comprising of Hexane: Benzene (1:1). Rf of spot coinciding with that of standard (2H4MB) (0.47) was eluted in solvent and UV spectrum was measured on a Perken-Elmer UV-Vis recording spectrophotometer UV-160. Maximum absorption was obtained at 278 nm.

Quantitative detection was done by GC. The constituent was confirmed by comparison with GC retention time of standard sample.

The concentrated volatiles were separated by GC, flame ionization detector (FID) with capillary column and GC-MS analysis using a Shimadzu, GC-14B coupled with QP 5000 MS system under the following conditions SPB-1 column (Supelco, USA, 30 m×0.32 mm, 0.25 µM film thickness); oven temperature programme, 60° C. for 2 min, rising at 2° C./min to 250° C., held for 5 min; injection port temperature 225° C.; detector temperature, 250° C.; carrier gas helium, flow rate 1 ml min$^{-1}$. The amount of solution injected was 1 µl for analysis.

The GC analysis indicated that the content of 2-hydrdxy-4 methoxy benzaldehyde in extracts as a metabolite as follows:

Whole tubers (A) 110 mg/g FW$^{-1}$ tubers without skin (B) 274 mg/g FW$^{-1}$; central core or medullary portion (C) 72.4 mg/g FW$^{-1}$ peel portion (D) 53.0 mg/g FW$^{-1}$ Suitability of Dichloromethane Fractions for Food Applications:

Dichloromethane has been reviewed by the International Agency for Research on Cancer (IARC. 1986. Monographs on the evaluation of the carcinogenic risk of chemicals to humans: Some halogenated hydrocarbons and pesticide exposures. *Lyon,* 41: 43-85). The maximum residue limits in food stuffs due to use of extractions solvents (dichloromethane) in preparation of flavourings from natural flavouring materials is 0.02 mg/kg.

Antioxidant assay using β-Carotene Linoleate model System (β CLAMS) (Hidalgo et al., 1994)

This is one of the rapid methods to screen antioxidants, which is mainly based on principle that Linoleic acid which is an unsaturated fatty acid gets oxidized by "*Reactive Oxgen Species*" (ROS) produced by oxygenated water. The products formed will initiate the β-Carotene oxidation, which leads to discoloration. This is prevented by antioxidants hence decrease in extent of discoloration indicates the activity i.e. more the discoloration, less will be the antioxidant activity and vice versa.

Due to insolubility of β-Carotene in water, it is first made into emulsion. β-Carotene is dissolved in chloroform and using Tween-40 (Polyoxyethylene sorbotan manonitrate) as surfactant, it was mixed with Linoleic acid to form emulsion. The resulting mixture is diluted with triple distilled water (1 part) and mixed well. This emulsion is further made up with oxygenated water (4 parts) which initiates the process of oxidation immediately. It is transferred to tubes containing samples. Initial (zero min) reading is read, followed by recording the absorbance at 15 min intervals at 470 nm. All tubes were placed in water bath at 50° C. throughout the experiment.

Materials:
β Carotene linoleic acid emulsion mixture—100 ml (Jayaprakash et al., 2000)

Composition of Emulsion:
0.4 mg β carotene, 40 mg linoleic acid and 400 mg tween-40 in 1 ml chloroform, which was removed under vacuum using the rotavapour (at 40° C.). This emulsion was mixed with 20 ml water & 80 ml of oxygenated water.

Preparation of extract solution: 4.5 mg/ml solution in ethanol was used for experiments.

BHA solution: 4.5 mg was dissolved 1-ml ethanol.

Method:
0.025, 0.05 and 0.1 ml of extract solution and 0.05 ml of BHA solution were added to separate tubes according to concentration (100 ppm, 50 ppm, 25 ppm) and volume was made up to 0.5 ml with ethanol. 4 ml of β Carotene Linolic acid emulsion was added to each tube. Absorbance of all samples were taken at 470 nm at Zero time and tubes were placed at 50° C. in water bath., Measurement of Absorbance was continued at an interval of 15 minutes, till the colour of β carotene disappeared in the control reaction (t=180 min). A mixture prepared as above without β Carotene emulsion served as blank and mixture without extract served as control. Dose response of antioxidant activity for various extracts was determined at different concentrations.

The antioxidant activity (% AA) of extracts was evaluated in terms of bleaching of β Carotene using the following formula (Hidalgo et al, 1994).

Each experiment was carried out in triplicate and the deviation of absorbance value was less than 10%.

$$\% AA = 100[1-(A^0-A^t)/A^0 0 - A^0 t)]$$

Where % AA=Antioxidant activity
$A^0$=Zero time absorbance of sample
$A^t$=Absorbance of sample after incubation for 180 min
$A^0 0$=Zero time absorbance of control
$A^t 0$=Absorbance of control after incubation for 180 min.
And results were expressed as % Antioxidant activity.

TABLE 1

| Extract | Concentration in ppm | % Activity ± S.D |
|---|---|---|
| A | 100 | 3.74 ± 1.135 |
|   | 500 | 10.59 ± 2.16 |
|   | 1000 | 14.28 ± 0.681 |
| B | 100 | 5.73 ± 0.486 |
|   | 500 | 16.08 ± 0.682 |
|   | 1000 | 29.63 ± 1.93 |
| C | 100 | 14.43 ± 1.43 |
|   | 500 | 28.05 ± 1.85 |
|   | 1000 | 43.46 ± 0.86 |
| D | 100 | 12.12 ± 1.23 |
|   | 500 | 35.14 ± 0.97 |
|   | 1000 | 45.70 ± 0.96 |
| Standard BHA | 100 | 84.3 |
|   | 500 | 88.6 |
|   | 1000 | 90.1 |

A = tubers with peel;
B = tubers without peel;
C = central core (medulla) portion of the tubers;
D = peel of tubers;
BHA = butylated hydroxy anisole The extracts of peel of the tubers showed good antioxidant activity compared to the whole tubers (on the basis of fresh weight). Even the central core or medullary extracts showed almost equal amount of antioxidant activity like the extracts of peel of tubers.

Example 2

Fresh tubers of *Decalepis hamiltonii* were collected from local market and sorted out to a required size (approximately 10.0±1.0 cm lengths and 2.0±0.5 cm diameters). The tubers were cleaned off extraneous matter and soil with 2-4 liters of cold water (15±2° C.)/1000 gm tubers. Later they were surface sterilized first with 200 ml of 70% alcohol for 5 seconds followed by washing with sterile water thrice. The surface of the tubers was blotted with sterilized blotting paper. The tubers (whole tubers (A) 606.35 gm; tubers without skin (B) 185 gm; central core or medullary portion (C) 72.40 gm; peel portion (D) 110 gm) were grounded into paste in mixer. The moisture content of the whole tubers and different parts of the tubers was recorded as: whole tubers (A) 74%; tubers without skin (B) 75%; central core or medullary portion (C) 40.23%; peel portion (D) 53.21%. Dichloromethane was added to the root paste (double to the weight of the sample) and left overnight in dark. Later the dichloromethane extract was separated by using the separating funnel. The same is repeated thrice with dichloromethane. Later all the dichloromethane fractions were pooled. Similarly different portions of the tubers were also separately extracted with dichloromethane after preparing their powder extract as said above (for the whole tuber). The same is air dried and finally dissolved in 1 ml ethanol and preserved in low temperature and dark for further analysis. The combined extracts were passed through a funnel containing anhydrous sodium sulphate to remove the water content, concentrated in a flash evaporator and dissolved in 1 ml ethanol and stored in closed vials. Quantification of the flavour compound was determined by gas chromatographic analysis (GC) using flame ionization detection (FID). All the alcohol extracts were finally analyzed for the flavor content 2-hydroxy-4-methoxy benzaldehyde by GC-MS.

Analysis of 2-hydroxy-4-methoxybenzaldehyde (2H4MB) was done by spotting the root extracts on TLC plate along with standard (Fluka Chemicals, Switzerland) and run in a solvent system comprising of Hexane: Benzene (1:1). Rf of spot coinciding with that of standard (2H4MB) (0.47) was eluted in solvent and UV spectrum was measured on a Perken-Elmer UV-Vis recording spectrophotometer UV-160. Maximum absorption was obtained at 278 nm. Quantitative detection was done by GC. The constituent was confirmed by comparison with GC retention time of standard sample.

The concentrated volatiles were separated by GC, flame ionization detector (FID) with capillary column and GC-MS analysis using a Shimadzu, GC-14B coupled with QP 5000 MS system Linder the following conditions SPB-1 column (Supelco, USA, 30 m×0.32 mm, 0.25 μM film thickness); oven temperature programme, 60° C. for 2 min, rising at 2° C./min to 250° C., held for 5 min; injection port temperature 225° C.; detector temperature, 250° C.; carrier gas helium, flow rate 1 ml min$^{-1}$. The amount of solution injected was 1 ul for analysis.

The GC analysis indicated that the content of 2-hydroxy-4 methoxy benzaldehyde in extracts as a metabolite as follows: whole tubers (A) 110 mg/g FW$^{-1}$ tubers without skin (B) 274 mg/g FW$^{-1}$; central core or medullary portion (C) 72.4 mg/g FW$^{-1}$ peel portion (D) 53.0 mg/g FW$^{-1}$ Suitability of Dichloromethane Fractions for Food Applications:

Dichloromethane has been reviewed by the International Agency for Research on Cancer (IARC. 1986. Monographs on the evaluation of the carcinogenic risk of chemicals to humans: Some halogenated hydrocarbons and pesticide exposures. *Lyon*, 41: 43-85). The maximum residue limits in food stuffs due to use of extractions solvents (dichloromethane) in preparation of flavourings from natural flavouring materials is 0.02 mg/kg.

Schematic representation of chemically stable radical scavenging activity using D.P.P.H as stable free radical: (Blios, 1958)

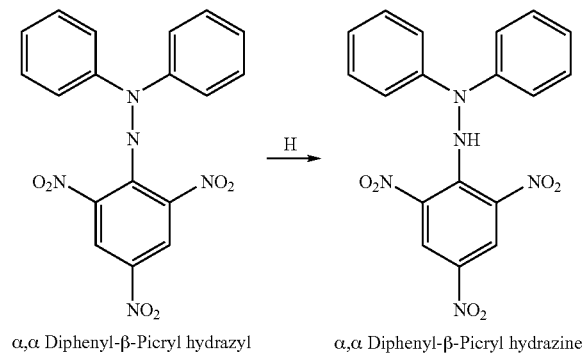

α,α Diphenyl-β-Picryl hydrazyl     α,α Diphenyl-β-Picryl hydrazine

Free radical scavenging potentials of the extracts were tested against a methanolic solution of α,α-diphenyl-β-picryl hydrazyl (D.P.P.H). Antioxidants reacts with D.P.P.H. and convert it to α,α-diphenyl-β-picryl hydrazine. The degree of discoloration indicates the scavenging potentials of the antioxidant extract. The change in the absorbance produced at 517 nm has been used as a measure of antioxidant activity.

Materials:

Methanolic solution of D.P.P.H (100 μM): 39.4 mg of D.P.P.H was dissolved in one liter of analytical grade methanol.

Preparation of the extract solutions: 55 mg of the extract was dissolved in 10 ml of methanol and filtered; the filtrate was used for the experiments.

Method:

Aliquots of 0.025, 0.05, 0.1 ml of extracts and standard were taken in different test tubes. To this 5 ml of methanolic solution of D.P.P.H was added, shaken well and the mixture was allowed to stand at room temperature for 20 minutes. The blank was prepared as above without extract. The readings were noted at 517 nm. The absorbance of blank was first noted at 517 nm. The change of absorbance of the samples was measured.

Scavenging activity was expressed as the inhibition percentage calculated using the following formula, $$\% \text{ Antiradical activity} = \frac{CONTROL_{Abs} - SAMPLE_{Abs} \times 100}{CONTROL_{Abs}}$$

TABLE 2

| Extract | Concentration in ppm | % Activity ± S.D |
|---|---|---|
| A | 100 | 4.3 ± 0.965 |
|   | 500 | 9.1 ± 1.325 |
|   | 1000 | 17.30 ± 1.286 |
| B | 100 | 18.75 ± 1.953 |
|   | 500 | 29.6 ± 1.226 |
|   | 1000 | 34.56 ± 0.985 |
| C | 100 | 26.90 ± 0.586 |
|   | 500 | 34.40 ± 1.269 |
|   | 1000 | 44.0 ± 1.56 |
| D | 100 | 20.1 ± 0.698 |
|   | 500 | 30.31 ± 1.569 |
|   | 1000 | 46.70 ± 1.236 |
| Standard D.P.P.H | 100 | 88.3 |
|   | 500 | 92.6 |
|   | 1000 | 94.3 |

A = tubers with peel;
B = tubers without peel;
C = central core (medulla) portion of the tubers;
D = peel of tubers;
BHA = butylated hydroxy anisole The extracts of peel of the tubers showed good antioxidant activity compared to the whole tubers (on the basis of fresh weight). Even the central core or medullary extracts showed almost equal amount of antioxidant activity like the extracts of peel of tubers.

Example 3

Fresh tubers of *Decalepis hamiltonii* were collected from local market and sorted out to a required size (approximately 10.0±1.0 cm lengths and 2.0±0.5 cm diameters). The tubers were cleaned off extraneous matter and soil with 2-4 liters of cold water (15±2° C.)/1000 gm tubers. Later they were surface sterilized first with 200 ml of 70% alcohol for 5 seconds followed by washing with sterile water thrice. The surface of the tubers was blotted with sterilized blotting paper. The tubers (whole tubers (A) 606.35 gm; tubers without skin (B)

185 gm; central core or medullary portion (C) 72.40 gm; peel portion (D) 110 gm) were grounded into paste in mixer. The moisture content of the whole tubers and different parts of the tubers was recorded as: whole tubers (A) 74%; tubers without skin (B) 75%; central core or medullary portion (C) 40.23%; peel portion (D) 53.21%. Dichloromethane was added to the root paste (double to the weight of the sample) and left overnight in dark. Later the dichloromethane extract was separated by using the separating funnel. The same is repeated thrice with dichloromethane. Later all the dichloromethane fractions were pooled. Similarly different portions of the tubers were also separately extracted with dichloromethane after preparing their powder extract as said above (for the whole tuber). The same is air dried and finally dissolved in 1 ml ethanol and preserved in low temperature and dark for further analysis. The combined extracts were passed through a funnel containing anhydrous sodium sulphate to remove the water content, concentrated in a flash evaporator and dissolved in 1 ml ethanol and stored in closed vials. Quantification of the flavour compound was determined by gas chromatographic analysis (GC) using flame ionization detection (FID). All the alcohol extracts were finally analyzed for the flavor content 2-hydroxy-4-methoxy benzaldehyde by GC-MS.

Analysis of 2-hydroxy-4-methoxybenzaldehyde (2H4MB) was done by spotting the root extracts on TLC plate along with standard (Fluka Chemicals, Switzerland) and run in a solvent system comprising of Hexane: Benzene (1:1). Rf of spot coinciding with that of standard (2H4MB) (0.47) was eluted in solvent and UV spectrum was measured on a Perken-Elmer UV-Vis recording spectrophotometer UV-160. Maximum absorption was obtained at 278 nm. Quantitative detection was done by GC. The constituent was confirmed by comparison with GC retention time of standard sample.

The concentrated volatiles were separated by GC, flame ionization detector (FID) with capillary column and GC-MS analysis using a Shimadzu, GC-14B coupled with QP 5000 MS system under the following conditions SPB-1 column (Supelco, USA, 30 m×0.32 mm, 0.25 µM film thickness); oven temperature programme, 60° C. for 2 min, rising at 2° C./min to 250° C., held for 5 min; injection port temperature 225° C.; detector temperature, 250° C.; carrier gas helium, flow rate 1 ml min$^{-1}$. The amount of solution injected was 1 µl for analysis:

The GC analysis indicated that the content of 2-hydroxy-4 methoxy benzaldehyde in extracts as a metabolite as follows:

Whole tubers (A) 110 mg/g FW$^{-1}$ tubers without skin (B) 274 mg/g FW$^{-1}$; central core or medullary portion (C) 72.4 mg/g FW$^{-1}$ peel portion (D) 53.0 mg/g FW$^{-1}$ Suitability of Dichloromethane Fractions for Food Applications:

Dichloromethane has been reviewed by the International Agency for Research on Cancer (IARC. 1986. Monographs on the evaluation of the carcinogenic risk of chemicals to humans: Some halogenated hydrocarbons and pesticide-exposures. *Lyon*, 41: 43-85). The maximum residue limits in food stuffs due to use of extractions solvents (dichloromethane) in preparation of flavorings from natural flavoring materials is 0.02 mg/kg.

Hydroxyl radical scavenging activity (Singhi, R. P., Chidambara Murthy, K. N., Jayaprakasha, G. K., Studies on the antioxidant activity of Pomegranate (*Punica grantum*) peel and seed extracts using in vitro models. J. of Agri. Food Chem., 2002, 50: 81-86)

Hydroxyl radicals have been implicated as highly damaging species in free radical pathology. This radical has the capacity to join nucleotides in DNA, cause strand breakage, which contributes to carcinogenesis, mutagenesis and cytotoxicity. In addition, this species is considered to be one of the initiators of lipid peroxidation process. Hence in the present method hydroxyl radical scavenging activity of the selected natural products were assessed by generating the hydroxyl radicals using ascorbic acid-Iron EDTA as the model.

The hydroxyl radicals formed by the oxidation react with DMSO to yield formaldehyde. The formaldehyde production from DMSO provides a convenient method to detect hydroxyl radicals formed during the oxidation of DMSO by the $Fe^{3+}$/ascorbic acid system was used to detect hydroxyl radicals.

Materials:
Iron-EDTA (1:2) mixture: 0.013 g of ammonium ferrous sulphate and 0.26 g of EDTA in 100 ml of water.
Ascorbic acid solution: 0.22 g in 100 ml distilled water.
1.70 ml dimethyl sulphoxide in 200 ml of phosphate buffer (pH 7.4).
17.5% trichloroacetic acid
EDTA Solution: 0.018 g in 100 ml distilled water
Nash Reagent: 2 M or 750 gms ammonium acetate+0.05 M or 3 ml acetic acid+0.02 M or 2 ml acetyl acetone in one liter of distilled water.

Based on the previous results three extracts which have shown significant activity that is methanolic extracts of grapes pomace, grape seed and pomegranate peel were selected for this model.

Method:
0.025, 0.05, 0.1 ml of the extracts are prepared in 2% alcohol were taken in different test tubes and evaporated on a water bath. To these, 1 ml of Iron-EDTA solution, 0.5 ml of EDTA and 1 ml of DMSO were added and the reaction was initiated by adding 0.5 ml of ascorbic acid to each of the test tubes. Test tubes were capped tightly and heated on water bath at 80-90° C. for 15 minutes. Then the reaction was terminated by the addition of 1 ml of ice-cold TCA (17.5% w/v) to all the test tubes, kept aside for 2 minutes and the formaldehyde formed was determined by the adding 3 ml of Nash reagent which was left for 10-15 minutes for colour development. Intensity of yellow colour formed was measured spectrophotometrically at 412 nm against reagent blank.

Percentage scavenging of Hydroxyl radicals were calculated by comparison of the results of the test compounds with that of the blank.

$$\% \text{ Hydroxyl radical Scavenging} = 1 - \frac{\text{Difference in absorbance of sample}}{\text{Difference in absorbance of blank}} \times 100$$

The necessary corrections were made for the absorbance of the test compounds. % Hydroxyl radical scavenging in calculated by the following formula,

TABLE 3

| Extract | Concentration in ppm | Concentration in µg | % Activity ± S.D |
|---|---|---|---|
| A | 100 | 0.1 | 31.99 ± 1.265 |
|   | 200 | 0.2 | 33.86 ± 0.968 |
| B | 100 | 0.1 | 23.40 ± 1.655 |
|   | 200 | 0.2 | 26.60 ± 2.01 |
| C | 100 | 0.1 | 35.4 ± 0.876 |
|   | 200 | 0.2 | 46.86 ± 1.112 |

TABLE 3-continued

| Extract | Concentration in ppm | Concentration in µg | % Activity ± S.D |
|---|---|---|---|
| D | 100 | 0.1 | 42.18 ± 0.689 |
|   | 200 | 0.2 | 48.26 ± 1.365 |

A = tubers with peel;
B = tubers without peel;
C = central core (medulla) portion of the tubers;
D = peel of tubers The extracts of peel of the tubers showed good antioxidant activity compared to the whole tubers (on the basis of fresh weight). Even the central core or medullary extracts showed almost equal amount of antioxidant activity like the extracts of peel of tubers.

The novelty of the present invention is, for the first time an antioxidant activity of tuberous root extracts of *D. hamiltonii* was determined and elucidated. And also it can serve as better antioxidant (since it can prevent more than one type of free radicals) unlike other synthetic antioxidants which can quench only one type of radical.

The main advantages of the present invention are:
1. The identification and reporting of antioxidant activity of dichloromethane extracts of tubers of *D. hamiltonii*.
2. On the basis of this study it is worthful to use *D. hamiltonii* tuberous root extracts for various pharmaceutical purposes in view of it's antioxidant nature against various free radicals like superoxide, and hydroxyl radicals. And also it can serve as better antioxidant (since it can prevent more than one type of free radicals) unlike other synthetic antioxidants which can quench only one type of radical.

We claim:

1. A method for preparing an antioxidant composition, comprising:
   extracting medulla and peel of a *Decalepis hamiltonii* tuberous root with dichloromethane to obtain an extract having antioxidant activity, and thereby preparing the antioxidant composition.

2. The method of claim 1 which further comprises concentrating the extract.

3. The method of claim 1 wherein the *Decalepis hamiltonii* tuberous root is surface sterilized by washing with 70% alcohol.

4. The method of claim 1 wherein in the step of extracting dichloromethane is present at a ratio of about 2:1 to the tuberous root by weight.

5. The method of claim 1 wherein the antioxidant activity ranges from 4-47% in an assay of antioxidant activity that comprises evaluating β-carotene bleaching, wherein % antioxidant activity is determined according to the formula:

$$\% \text{ antioxidant activity} = 100[1-(A^0-A^t)/A^00-A^t0)]$$

wherein:
$A^0$ = zero time absorbance at 470 nm of a sample comprising the extract having antioxidant activity and an oxygenated aqueous β-carotene linoleic acid emulsion,
$A^t$ = absorbance at 470 nm of the sample after incubation for a time period t,
$A^00$ = zero time absorbance at 470 nm of a control comprising the oxygenated aqueous β-carotene linoleic acid emulsion without the extract, and
$A^t0$ = absorbance at 470 nm of the control after incubation for the time period t.

6. A method for preparing an antioxidant composition, comprising:
   extracting medulla and peel of a *Decalepis hamiltonii* tuberous root with dichloromethane to obtain an extract having antioxidant activity, wherein the antioxidant activity comprises free radical scavenging activity; and
   concentrating the extract, and thereby preparing the antioxidant composition.

7. The method of claim 6 wherein the free radical scavenging activity comprises hydroxyl radical scavenging activity.

8. The method of claim 6 wherein the antioxidant composition is selected from:
   (a) an antioxidant composition in which the extract is present in a concentration range of 500 ppm to 1,000 ppm, the composition having antioxidant activity of 30 to 45% when evaluated in an assay that comprises evaluating β-carotene bleaching, wherein % antioxidant activity is determined according to the formula:

$$\% \text{ antioxidant activity} = 100[1-(A^0-A^t)/A^00-A^t0)]$$

wherein:
   $A^0$ = zero time absorbance at 470 nm of a sample comprising the extract having antioxidant activity and an oxygenated aqueous β-carotene linoleic acid emulsion,
   $A^t$ = absorbance at 470 nm of the sample after incubation for a time period t,
   $A^00$ = zero time absorbance at 470 nm of a control comprising the oxygenated aqueous β-carotene linoleic acid emulsion without the extract, and
   $A^t0$ = absorbance at 470 nm of the control after incubation for the time period t,
   (b) an antioxidant composition in which the extract is present in a concentration range of 500 ppm to 1,000 ppm, the composition having antioxidant activity of 35 to 46% when tested in an assay of antioxidant activity that comprises determining free radical scavenging activity by measuring absorbance at 517 nm of a methanolic solution of α,α-diphenyl-β-picryl hydrazyl, wherein % free radical scavenging activity is determined according to the formula:

$$\% \text{ free radical scavenging activity} = [(A_c-A_s)/A_c] \times 100,$$

wherein:
   $A_c$ is absorbance at 517 nm of a methanolic α,α-diphenyl-β-picryl hydrazyl solution without the extract, and
   $A_s$ is absorbance at 517 nm of a methanolic α,α-diphenyl-β-picryl hydrazyl solution with the extract,
   (c) an antioxidant composition in which the extract is present in a concentration range of 100 ppm to 200 ppm, the composition having antioxidant activity of 36 to 47% when tested in an assay of antioxidant activity that comprises determining hydroxyl scavenging activity by detecting a percentage of formaldehyde that is formed from hydroxyl radical-induced oxidation of DMSO when the extract is present relative to formaldehyde that is formed from hydroxyl radical-induced oxidation of DMSO when the extract is absent,
   (d) an antioxidant composition in which the extract is present in a concentration range of 500 ppm to 1,000 ppm and that has antioxidant activity of 36 to 47% in the assay of antioxidant activity as in (a),
   (e) an antioxidant composition in which the extract is present in a concentration range of 500 ppm to 1,000 ppm and that has antioxidant activity of 32 to 48% in the assay of antioxidant activity as in (b), and
   (f) an antioxidant composition in which the extract is present in a concentration range of 100 ppm to 200 ppm and that has antioxidant activity of 43 to 49% in the assay of antioxidant activity as in (c).

9. A method for preparing an antioxidant pharmaceutical composition, comprising:
  extracting medulla and peel of Decalepis hamiltonii tuberous roots with dichloromethane to obtain an extract having antioxidant activity; and
  mixing the extract having antioxidant activity with a pharmaceutically acceptable excipient or an edible item, and thereby preparing the antioxidant pharmaceutical composition.

10. The method of claim 9 wherein the antioxidant activity comprises free radical scavenging activity.

11. The method of claim 10 wherein the free radical scavenging activity comprises hydroxyl radical scavenging activity.

12. The method of claim 9 wherein the antioxidant activity ranges from 4-47% in an assay of antioxidant activity that comprises evaluating β-carotene bleaching, wherein % antioxidant activity is determined according to the formula:

% antioxidant activity=$100[1-(A^0-A^t)/A^00-A^t0)]$ wherein:
  $A^0$=zero time absorbance at 470 nm of a sample comprising the extract having antioxidant activity and an oxygenated aqueous β-carotene linoleic acid emulsion,
  $A^t$=absorbance at 470 nm of the sample after incubation for a time period t,
  $A^00$=zero time absorbance at 470 nm of a control comprising the oxygenated aqueous β-carotene linoleic acid emulsion without the extract, and
  $A^t0$=absorbance at 470 nm of the control after incubation for the time period t.

13. The method of claim 9 wherein the antioxidant pharmaceutical composition is selected from the group consisting of
  (a) a pharmaceutical composition in which the extract is present in a concentration range of 100 ppm to 1,000 ppm,
  (b) a pharmaceutical composition in which the extract is present in a concentration range of 500 ppm to 1,000 ppm, the pharmaceutical composition having antioxidant activity of 30 to 45% when evaluated in an assay that comprises evaluating β-carotene bleaching, wherein % antioxidant activity is determined according to the formula:

% antioxidant activity=$100[1-(A^0-A^t)/A^00-A^t0)]$ wherein:
  $A^0$=zero time absorbance at 470 nm of a sample comprising the extract having antioxidant activity and an oxygenated aqueous β-carotene linoleic acid emulsion,
  $A^t$=absorbance at 470 nm of the sample after incubation for a time period t,
  $A^00$=zero time absorbance at 470 nm of a control comprising the oxygenated aqueous β-carotene linoleic acid emulsion without the extract, and
  $A^t0$=absorbance at 470 nm of the control after incubation for the time period t,
  (c) a pharmaceutical composition in which the extract is present in a concentration range of 500 ppm to 1,000 ppm, the pharmaceutical composition having antioxidant activity of 35 to 46% when tested in an assay of antioxidant activity that comprises determining free radical scavenging activity by measuring absorbance at 517 nm of a methanolic solution of α,α-diphenyl-β-picryl hydrazyl, wherein % free radical scavenging activity is determined according to the formula:

% free radical scavenging activity=$[(A_c-A_s)/A_c] \times 100$, wherein:
  $A_c$ is absorbance at 517 nm of a methanolic α,α-diphenyl-β-picryl hydrazyl solution without the extract, and
  $A_s$ is absorbance at 517 nm of a methanolic α,α-diphenyl-β-picryl hydrazyl solution with the extract,
  (d) a pharmaceutical composition in which the extract is present in a concentration range of 100 ppm to 200 ppm, the pharmaceutical composition having antioxidant activity of 36 to 47% when tested in an assay of antioxidant activity that comprises determining hydroxyl scavenging activity by detecting a percentage of formaldehyde that is formed from hydroxyl radical-induced oxidation of DMSO when the extract is present relative to formaldehyde that is formed from hydroxyl radical-induced oxidation of DMSO when the extract is absent,
  (e) a pharmaceutical composition in which the extract is present in a concentration range of 500 ppm to 1,000 ppm and that has antioxidant activity of 36 to 47% in the assay of antioxidant activity as in (b),
  (f) a pharmaceutical composition in which the extract is present in a concentration range of 500 ppm to 1,000 ppm and that has antioxidant activity of 32 to 48% in the assay of antioxidant activity as in (c), and
  (g) a pharmaceutical composition in which the extract is present in a concentration range of 100 ppm to 200 ppm and that has antioxidant activity of 43 to 49% in the assay of antioxidant activity as in (d).

* * * * *

UNITED STATES PATENT AND TRADEMARK OFFICE
CERTIFICATE OF CORRECTION

| | |
|---|---|
| PATENT NO. | : 8,323,704 B2 |
| APPLICATION NO. | : 10/585226 |
| DATED | : December 4, 2012 |
| INVENTOR(S) | : Kotamballi Nagendra Murthy Chidambara Murthy et al. |

It is certified that error appears in the above-identified patent and that said Letters Patent is hereby corrected as shown below:

In the Claims

Column 13, Line 27:

"$A^t0$=zero time absorbance at 470 nm of a control" should read, --$A°0$=zero time absorbance at 470 nm of a control--.

Signed and Sealed this
Sixth Day of August, 2013

Teresa Stanek Rea
*Acting Director of the United States Patent and Trademark Office*